(12) United States Patent
Phillips et al.

(10) Patent No.: US 10,465,242 B2
(45) Date of Patent: Nov. 5, 2019

(54) MULTI-SEQUENCE CAPTURE SYSTEM

(71) Applicant: University of Utah Research Foundation, Salt Lake City, UT (US)

(72) Inventors: John Phillips, Salt Lake City, UT (US); William M. Hanson, Salt Lake City, UT (US); Jennifer M. Heemstra, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 139 days.

(21) Appl. No.: 15/650,832

(22) Filed: Jul. 14, 2017

(65) Prior Publication Data

US 2018/0057874 A1   Mar. 1, 2018

Related U.S. Application Data

(60) Provisional application No. 62/393,592, filed on Sep. 12, 2016, provisional application No. 62/362,288, filed on Jul. 14, 2016.

(51) Int. Cl.
| | |
|---|---|
| *C12Q 1/6874* | (2018.01) |
| *C12Q 1/6806* | (2018.01) |
| *C12Q 1/6876* | (2018.01) |
| *C12Q 1/6816* | (2018.01) |

(52) U.S. Cl.
CPC ......... *C12Q 1/6874* (2013.01); *C12Q 1/6806* (2013.01); *C12Q 1/6816* (2013.01); *C12Q 1/6876* (2013.01)

(58) Field of Classification Search
None
See application file for complete search history.

(56) References Cited

U.S. PATENT DOCUMENTS

| | | |
|---|---|---|
| 6,743,905 B2 | 6/2004 | Woo et al. |
| 7,074,569 B2 | 7/2006 | Woo et al. |
| 7,211,654 B2 | 5/2007 | Gao et al. |
| 7,553,958 B2 | 6/2009 | Gao et al. |

(Continued)

OTHER PUBLICATIONS

Iwai et al.; "5'-Levulinyl and 2'-tetrahydrofuranyl protection for the synthesis of oligoribonucleotides by the phosphoramidite approach"; Nucleic Acids Research; (Oct. 25, 1988); pp. 9443-9456; vol. 16, No. 20; Japan.

(Continued)

*Primary Examiner* — Kaijiang Zhang
(74) *Attorney, Agent, or Firm* — Thorpe North & Western, LLP

(57) ABSTRACT

Systems, devices, and methods for capturing single source-specific biological material from a multi-source aggregate of biological material are disclosed and discussed. A capture system is generated using reversible chain-blocking to make capture substrates having substrate-linked populations of capture molecules specific for molecules of interest. Incubating such capture substrates in the presence of only a single source of biological material facilitates the association of molecules of interest from the same source. Capture substrate-specific barcode sequences coupled to the capture molecules allow multisource aggregate processing and subsequent grouping to retain the source-specific information following downstream processing.

13 Claims, 9 Drawing Sheets

Specification includes a Sequence Listing.

(56) References Cited

U.S. PATENT DOCUMENTS

| | | | |
|---|---|---|---|
| 7,615,629 B2 * | 11/2009 | Arar | C07H 21/04 536/116 |
| 7,807,807 B2 | 10/2010 | Gao et al. | |
| 7,897,338 B2 | 3/2011 | Woo et al. | |
| 7,928,207 B2 | 4/2011 | Bodepudi et al. | |
| 8,053,187 B2 | 11/2011 | Gao et al. | |
| 8,138,330 B2 | 3/2012 | Leuck et al. | |
| 8,461,317 B2 | 6/2013 | Gao et al. | |
| 8,481,698 B2 | 7/2013 | Lieberman et al. | |
| 9,303,055 B2 | 4/2016 | Gao et al. | |
| 2007/0026434 A1 | 2/2007 | Woo et al. | |
| 2007/0219361 A1 | 9/2007 | Bodepudi et al. | |
| 2008/0269068 A1 | 10/2008 | Church et al. | |
| 2011/0160082 A1 | 6/2011 | Woo et al. | |
| 2013/0274117 A1 | 10/2013 | Church et al. | |
| 2015/0031555 A1 | 1/2015 | Johnson et al. | |
| 2015/0154352 A1 | 6/2015 | Johnson et al. | |
| 2015/0344871 A1 | 12/2015 | Johnson et al. | |
| 2016/0122753 A1 | 5/2016 | Mikkelsen et al. | |

OTHER PUBLICATIONS

Katajisto et al.; "Solid-Phase Synthesis of Oligonucleotide Glycoconjugates Bearing Three Different Glycosyl Groups: Orthogonally Protected Bis(hydroxymethyl)-N,N '-bis(3-hydroxypropyl)malondiamide Phosphoramidite as Key Building Block"; The Journal of Organic Chemistry; (Oct. 29, 2004); pp. 7609-7615; vol. 69, No. 22; American Chemical Society; <doi:10.1021/jo048984o >.

Katolik et al.; "Regiospecific Solid-Phase Synthesis of Branched Oligoribonucleotides That Mimic Intronic Lariat RNA Intermediates"; The Journal of Organic Chemistry; (2014); pp. 963-975; vol. 79, No. 3; ACS Publications.

Lackey et al.; "Acetal Levulinyl Ester (ALE) Groups for 2'-Hydroxyl Protection of Ribonucleosides in the Synthesis of Oligoribonucleotides on Glass and Microarrays"; Journal of American Chemical Society; (Jun. 24, 2009); pp. 8496-8502; vol. 131, No. 24; <doi: 10.1021/ja9002074 >.

Lackey et al.; "The acetal levulinyl ester (ALE) group for the 2'-hydroxyl protection of ribonucleosides and the synthesis of oligoribonucleotides"; Nucleic Acids Symposium Series; (Sep. 8, 2008); pp. 35-36; No. 52; Oxford University Press <doi: 10.1093/nass/nrn018 >.

Macosko et al.; "Drop-Seq Laboratory Protocol"; Harvard Medical School; (Dec. 28, 2015); 20 pages; Version 3.1, Steve McCarroll's lab <URL: www.mccarrolllab.com/dropseq >.

Macosko et al.; "Highly Parallel Genome-wide Expression Profiling of Individual Cells Using Nanoliter Droplets"; Cell; (May 21, 2015); pp. 1202-1214; vol. 161, Issue 5, Elsevier Inc.

Reddy et al.; "Facile Access to 5'-S-(4,4'-Dimethoxytrityl)-2',5'-Dideoxyribonucleosides via Stable Disulfide Intermediates"; Current Protocols in Nucleic Acid Chemistry; (Sep. 1, 2015); pp. 1.34.1-1.34; vol. 62; <doi: 10.1002/0471142700.nc0134s62 >.

Ueno et al.; "Synthesis of 3'-3'-linked oligonucleotides branched by a pentaerythritol linker and the thermal stabilities of the triplexes with single-stranded DNA or RNA"; Bioconjugate Chemistry; May-Jun. 2003); pp. 684-689; vol. 14, No. 3; American Chemical Society; <doi: 10.1021/bc020059q >.

* cited by examiner

FIGs. 3A-C

SEQUENCE LISTING

<160> NUMBER OF SEQ ID NOS: 9

<210> SEQ ID NO 1
<211> LENGTH: 77
<212> TYPE: DNA
<213> ORGANISM: Homo sapiens
<220> FEATURE:
<221> NAME/KEY: misc_feature
<222> LOCATION: (33)..(52)
<223> OTHER INFORMATION: n is a, c, g, or t

<400> SEQUENCE: 1
tttttttaag cagtggtatc aacgcagagt acnnnnnnnn nnnnnnnnnn nntggtgaat    60
aggcagacag acttgtc                                                  77

<210> SEQ ID NO 2
<211> LENGTH: 73
<212> TYPE: DNA
<213> ORGANISM: Homo sapiens
<220> FEATURE:
<221> NAME/KEY: misc_feature
<222> LOCATION: (33)..(52)
<223> OTHER INFORMATION: n is a, c, g, or t

<400> SEQUENCE: 2
tttttttaag cagtggtatc aacgcagagt acnnnnnnnn nnnnnnnnnn nntgagaccc    60
tcaggcggct gct                                                      73

<210> SEQ ID NO 3
<211> LENGTH: 20
<212> TYPE: DNA
<213> ORGANISM: Homo sapiens

<400> SEQUENCE: 3
gcacatatga caccagtgag                                               20

<210> SEQ ID NO 4
<211> LENGTH: 22
<212> TYPE: DNA
<213> ORGANISM: Homo sapiens

<400> SEQUENCE: 4
agagtctctc agctggtaca cg                                            22

<210> SEQ ID NO 5
<211> LENGTH: 22
<212> TYPE: DNA
<213> ORGANISM: Homo sapiens

<400> SEQUENCE: 5
actacacctc atccactatt cc                                            22

<210> SEQ ID NO 6
<211> LENGTH: 20
<212> TYPE: DNA
<213> ORGANISM: Homo sapiens

<400> SEQUENCE: 6
cagagaaggg agatctttcc                                               20

<210> SEQ ID NO 7
<211> LENGTH: 23
<212> TYPE: DNA
<213> ORGANISM: Homo sapiens

```
<400> SEQUENCE: 7
aggcagtatc tggagtcatt gag                                             23

<210> SEQ ID NO 8
<211> LENGTH: 188
<212> TYPE: DNA
<213> ORGANISM: Homo sapiens

<400> SEQUENCE: 8
cgtttctctg tgaacttcca gaaagcagcc aaatccttca gtctcaagat ctcagactca     60
cagctggggg atgccgcgat gtatttctgt gcttatagga gcgcggtcaa tgccagactc    120
atgtttggag atggaactca gctggtggtg aagcccaata tccagaagcc tgaccctgcc    180
gtgtacca                                                             188

<210> SEQ ID NO 9
<211> LENGTH: 348
<212> TYPE: DNA
<213> ORGANISM: Homo sapiens

<400> SEQUENCE: 9
ttttcccctg accctggagt ctgccaggcc ctcacatacc tctcagtacc tctgtgccag     60
cagtgaagct cgggggctag cggagttcac agatacgcag tattttggcc caggcacccg    120
gctgacagtg ctcgaggacc tgaaaaacgt gttcccaccc gaggtcgctg tgtttgagcc    180
atcagaagca gagatctccc acacccaaaa ggccacactg gtgtgcctgg ccacaggctt    240
ctaccccgac cacgtggagc tgagctggtg ggtgaatggg aaggaggtgc acagtggggt    300
cagcacagac ccgcagcccc tcaaggagca gcccgccctc aatgactc                 348
```

MULTI-SEQUENCE CAPTURE SYSTEM

CROSS-REFERENCE TO RELATED APPLICATIONS

This application claims the benefit of U.S. Provisional Patent Application No. 62/362,288, filed on Jul. 14, 2016, and U.S. Provisional Patent Application No. 62/393,592, filed on Sep. 12, 2016, both of which are incorporated herein by reference.

GOVERNMENT LICENSE RIGHTS

This invention was made with government support under grant numbers DK020503, DK090257, and GM116991 awarded by the National Institutes of Health, and under grant numbers 1308364 and 1608561, awarded by the National Science Foundation. The government has certain rights in the invention.

BACKGROUND

The immune system is comprised of many biological structures and processes within a subject, such as a human, that protects against disease. This system must detect a wide variety of pathogens, such as bacteria, viruses, parasitic worms, and the like, which are distinguishable from the subject's own tissue. Pathogens can rapidly evolve and adapt, and thereby avoid detection and neutralization by the immune system; however, multiple defense mechanisms have also evolved to recognize and neutralize such pathogens. Humans, for example, have sophisticated defense mechanisms, including the ability to adapt over time to recognize specific pathogens more efficiently. Adaptive (or acquired) immunity creates immunological memory after an initial response to a specific pathogen, leading to an enhanced response to subsequent encounters with that same pathogen.

BRIEF DESCRIPTION OF THE DRAWINGS

For a fuller understanding of the nature and advantage of the present disclosure, reference is being made to the following detailed description of embodiments and in connection with the accompanying drawings, in which.

DESCRIPTION OF EMBODIMENTS

Figure 1A:
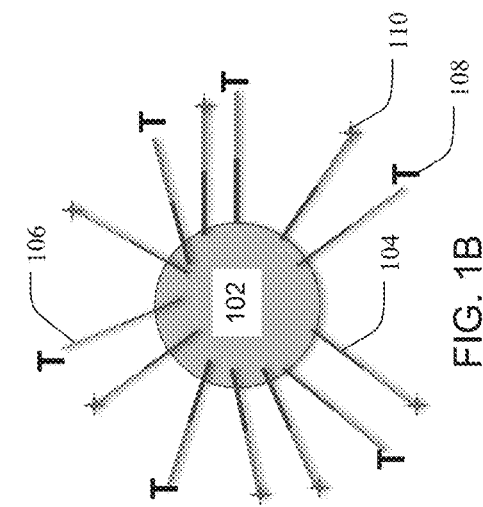
FIG. 1A is schematic illustrating a capture system in accordance with an embodiment of the present disclosure.

Although the following detailed description contains many specifics for the purpose of illustration, a person of ordinary skill in the art will appreciate that many variations and alterations to the following details can be made, and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals appearing in different drawings represent the same or similar element. Numbers provided in flow charts, processes, and the like, are provided for clarity in illustrating steps and operations, and do not necessarily indicate a particular order or sequence.

Furthermore, the described features, structures, techniques, or characteristics can be combined in any suitable manner in one or more embodiments. In the following description, numerous specific details are provided in order to provide a thorough understanding of various embodiments. One skilled in the relevant art will recognize, however, that such detailed embodiments do not limit the overall concepts articulated herein, but are merely representative thereof. One skilled in the relevant art will also recognize that the technology can be practiced without one or more of the specific details, or with other methods, components, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, compositional elements, materials, and/or the like, may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Additionally, it is intended that support is provided by such lists for the list as a whole, an individual item from the list, and any selection or grouping of items from the list.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

Example Embodiments

An initial overview is provided below, and specific embodiments are then described in further detail. This initial summary is intended to aid readers in understanding the technology more quickly, but is not intended to identify key or essential technological features, nor is it intended to limit the scope of the claimed subject matter.

The widespread availability of next-generation sequencing (NGS) instruments has enabled researchers around the world to examine organisms at unprecedented levels of detail at low cost, resulting in a rapid escalation of NGS-based studies. Current technologies generally require large amounts of template material, which is produced from samples containing millions of cells. While data generated using this approach gives a view of the population-wide characteristics of these cells, it provides no mechanism for linking information to individual cells. As a result, it is not possible to directly examine the distribution of variation across large populations of cells within a sample. Due to this limitation, variation that is present at a low frequency within a population of cells may not be easily discriminated from sequencing noise. Furthermore, population-based techniques do not allow the direct examination of fluctuations of the relative frequency of variation within a population of cells over time. These deficiencies of prior NGS technologies have posed a particularly large challenge for research examining, for example, cancer stem cells, which occur at a low frequency in tumors, but are thought to be central to tumor survival and treatment escape.

In an attempt to overcome these obstacles, single-cell analysis techniques have been developed, such as, for example, drop sequence (drop-seq) techniques. Generally, drop-seq describes techniques whereby individual cells are incubated with an mRNA capture bead in nanoliter droplets, thus enabling down-stream sequencing of all specific mRNA captured on a single bead from that cell. While drop-seq methods have achieved some progress in circumventing limitations of population-wide studies, they remain limited by short read length sequencing platforms where sequences containing the critical information are distant from the 3' end of the message. Additionally, current drop-seq technology only enables specific, cell identifying, barcoding of mRNA captured by the polyadenylation portion of the molecule.

Obtaining specific sequence information from distinct locations within, for example, an mRNA for multiple different mRNA or other molecules of interest from a single cell would be of significant value for a variety of uses. Nonlimiting examples can include measuring the ratio of differentially spliced messages in individual cancer stem cells, obtaining the paired sequences of heavy and light chains in antigen receptors, and the like.

As such, various assay techniques can have greater utility if two or more different molecules of interest (e.g. molecules, sequences, etc.) from each cell could be captured and associated for analysis following downstream processing, such as NGS, for example. Such associating of molecules of interest can be a physical association, an informational association, or a combination thereof. In some examples, the association can be substrate-specific, such that specific molecules that have been captured and processed can be correlated back to a specific substrate, and thus the specific cell or cells from which they came. In one example, a reversible chain blocking protecting group can be used to create various substrates, or capture substrates, (e.g. beads, etc.) having at least two distinct capture complexes to capture distinct molecules of interest, multiple distinct regions of a molecule of interest, or the like. Nonlimiting examples can include oligonucleotide sequences, including DNA and RNA sequences, mRNA splice junctions, gene specific variants of an mRNA, diversity regions of paired chain receptors, and the like. Any molecule of interest that can be captured according to the present technology is considered to be within the present scope. In some examples, capture complexes can include distinct bar-coded regions for tracking or other useful purposes, and can further include a capture molecule coupled thereto, or in other words, a molecule capable of capturing a molecule of interest. In one example of single cell analysis within a pool of biological material taken from a population of cells, barcodes originating from a given capture substrate can be tracked to determine which cellular data corresponds to a cell or cells of interest originally associated with that substrate. Such multi-sequence capture substrates can thus be used to, among other things, isolate and amplify at least two different molecules of interest while maintaining the pairing information for these molecules.

In one nonlimiting example, the present technology can be applied to any heterodimeric (multimeric) complex where the pairing of exact sequences of the components of that complex is desirable. In a more specific example, such a complex can be a multimeric receptor, and thus it may be useful to determine the exact genetic sequences of components of the receptor from the same cell. Various nonlimiting multimeric examples can include T-cell receptors, B-cell receptors, IL-2 receptors, nuclear hormone receptors, integrins, and the like, including combinations thereof. Furthermore, it is additionally contemplated that the presently disclosed technology can be utilized to pair or otherwise link receptors, surface proteins, and other distinct biomarker sequences from the same cell. In one non-limiting example, sequences of stem cell surface markers can be linked and assayed to determine single cell variation across a stem cell population.

It is noted that, while much of the following disclosure is related to capture beads and immunogenic cells, it is intended that the present scope extend to any device, method, system, assay, cell, cell type, biological material source, or the like, that can benefit from the disclosed technology. In other words, the following description of multi-sequence capture beads utilized in a drop-sequence (drop-seq) process is merely providing one example to facilitate an understanding of the disclosed technology, and is not intended to be limiting.

As one specific example, the antigen receptors on individual lymphocytes control their specificity and are critical components in disease outcome. These receptors are created by somatic gene rearrangements at two loci on different chromosomes to produce heavy and light chains that assemble to generate a T cell receptor (αβ TCR or γδ TCR). The determinant of antigen specificity is the rearrangement of variable (V), diversity (D), and joining (J) segments that make up the complementarity determining region (CDR3). The antigen receptor VDJ sequence for each chain lies adjacent to a locus-specific constant domain, enabling capture from the total cellular RNA using primers specific for this sequence. Subsequent primer extension and PCR amplification can then allow complete chain sequence assembly from short NGS reads. Obtaining the paired heavy and light chain antigen receptor sequences for each of the ~$10^{12}$ lymphocytes in the human body, combined with their abundance and activation status, can allow powerful system-level examination of human pathologies and disease. While current single-cell analyses of this type are extremely laborious, constraining throughput to hundreds of cells, the presently disclosed technology can facilitate such a level of examination.

In one non-limiting example, capture substrates, such as capture beads, can include capture complexes that include capture molecules (or capture sequences) having binding sequences for each of the mRNAs encoding the dimeric T-cell receptor. In this non-limiting example, the TCRα and TCRβ sequences have been selectively targeted from total T-cell RNA; however, the TCRγ and TCRδ sequences can also be selectively targeted, either with or without one or more of the TCRα and TCRβ sequences. This approach thus enables reverse transcription and PCR amplification of the specific portions of the mRNAs that lead to the incredible diversity that comprises this portion of the cellular immune system. The capture complexes can include a barcoded region that is coded to the capture substrate to which they are coupled, in this case for both the heavy and light chain mRNAs. Because they are coupled to the same capture substrate, paired sequence information for TCRα and TCRβ sequences can be obtained for a single cell. Such can be useful in various applications, such as, for example, identifying T-cell clones that give rise to autoimmune diseases, establishing the dynamics of an immune response, measuring the ratios of mRNA splice variants in cancer stem cells, and the like.

Figure 1B:
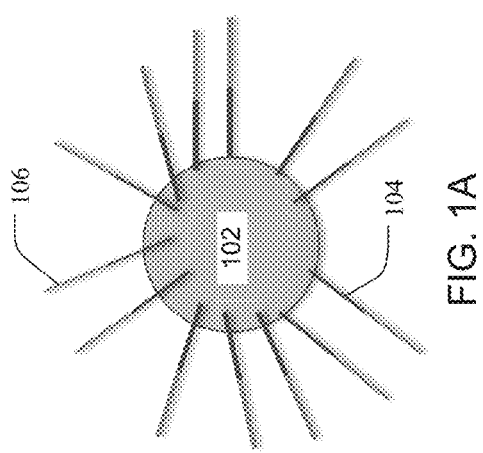
FIG. 1B is schematic illustrating a capture system in accordance with an embodiment of the present disclosure.
Figure 1C:
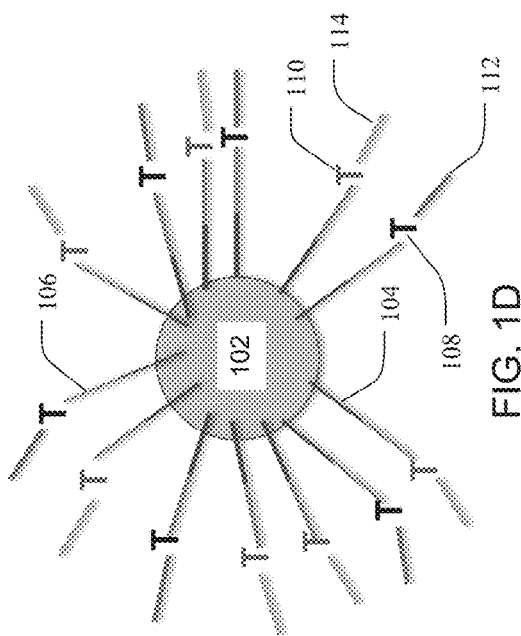
FIG. 1C is schematic illustrating a capture system in accordance with an embodiment of the present disclosure.

A simplified example is shown in FIG. 1A-D. FIG. 1A shows a substrate 102 having platform-specific sequence 104 coupled to the substrate 102, and a barcode sequence 106 coupled to a platform-specific sequence 104. A building block, such as a nucleoside phosphoramidite building block, for example, can be used to build onto each capture complex. In FIG. 1B, for example, dimethoxytrityl (DMT)-protected nucleoside phosphoramidite 108 and a levulinyl (Lev)-protected nucleoside phosphoramidite 110 are used, and have been coupled to the barcode sequences 106. In this example, the DMT-protected phosphoramidite 108 and the Lev-protected phosphoramidite 110 are show as a 50/50 mixture, which can be adjusted by adjusting the proportion of each protected nucleoside phosphoramidite component in the reaction mixture. The ratio of components, whether there are two, or more than two, can vary depending on the design of a given system, assay, analytic process, or the like, and should not be seen as limiting. For example, the ratio of the given capture molecules on a capture substrate can vary depending on differing amounts of the molecules of interest needed for each capture molecule, or the diversity of molecules of interest for a given capture molecule. If, for example, an assay that is merely determining the presence or absence of one molecule of interest having a very low diversity against a background of another molecule of interest having a high diversity would likely benefit from a ratio of high diversity to low diversity capture molecules that is high. In other words, fewer capture molecules are needed to detect the presence of a molecule that has a low diversity compared to a molecule that has a high diversity. Various ratios are contemplated, and are considered to be nonlimiting. Specific examples, however, can include ratio ranges of from 1:100 to 100:1, 1:10 to 10:1, 1:4 to 4:1, and the like, including specific ratios within these ranges.

Figure 1D:
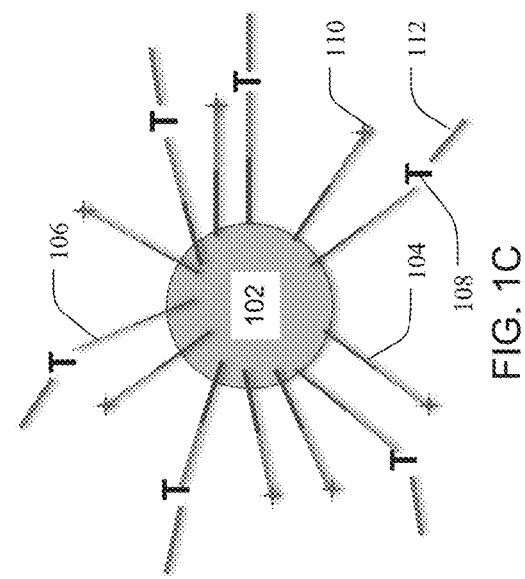
FIG. 1D is schematic illustrating a capture system in accordance with an embodiment of the present disclosure.

Returning to FIG. 1C, capture complexes having DMT protection 108 are deprotected, and first capture molecules (or capture sequences) 112 are built or sequenced on the exposed nucleoside phosphoramidite. In the specific example of T cell receptors, this first capture molecule could be an alpha-specific sequence or a beta-specific sequence. As is shown in FIG. 1D, the Lev-protected phosphoramidite 110 is then deprotected, and second capture molecules (e.g. capture sequences) 114 are built or sequenced on the now-exposed nucleoside phosphoramidite previously protected by Lev 110. As described above, if the first capture molecule 112 was an alpha-specific sequence, then the second capture molecule would be a beta-specific sequence, and vice versa.

As this example illustrates, specific beads can be designed and made having multiple capture complexes attached to a given substrate though a process of coupling with a mixture of 108 and 110, selective deprotection of 108 and synthesis of a sequence, then deprotection of 110 and coupling with a mixture of 108 and 110, and so on. The capture complexes associated with a given bead can be contacted with nucleic acids from a single cell, and tracked through biotechnological processing to the data processing stage. In this way, any number of molecules of interest, depending on the number of distinct capture complex types on the substrate, can be assayed for this single cell.

Paired or otherwise associated molecular information extracted from multiple-source samples or aggregates having can be obtained using various methodologies, such as drop-seq, for example. Depending on experimental design, the associated molecular information may or may not be associated with a single cell. For sequence information, for example, such can be accomplished via the construction and/or use of capture substrates having at least two different distinct groups of capture complexes having capture molecules of primer sequences attached to capture substrate-specific unique barcodes that allow chain reconstruction from short read-length NGS platforms.

While various techniques (e.g. photolabile techniques, acid/base labile techniques, and the like) for creating such capture substrates are contemplated, in one example a phosphoramidite monomer can be utilized that reversibly blocks chain extension to enable divergent synthesis of two or more capture molecules (e.g., primer sequences) on each barcoded bead. In one example, a method of making a multi-probe capture system can include synthesizing a plurality of barcode sequences extending from a capture substrate, where the plurality of barcode sequences includes a specific identifier to the capture substrate on which they were synthesized. The barcode sequences can be synthesized from any precursor, such as a portion of the capture substrate material, a coating or particles embedded in a coating applied to the substrate material, a platform-specific molecule or sequence associated with a specific capture substrate, or any linking molecule coupled to the capture substrate. In other examples, barcode sequences can be synthesized apart from the capture substrate, and subsequently coupled thereto.

A first portion of the plurality of barcode sequences is then protected with a first protecting group, and a second portion of the plurality of barcode sequences is protected with a second protecting group. The first and second portions of barcodes can be protected simultaneously in some examples, and sequentially in other examples. In some cases the second protecting group can be any protecting group, protection chemistry, or the like, that is stable under conditions for deprotection of the first protecting group, stable under conditions for oligonucleotide synthesis, and is capable of deprotection under conditions compatible with oligonucleotides.

The method can next comprise deprotecting the first portion of the plurality of barcode sequences by removing the first protecting group, followed by synthesizing a plurality of first oligonucleotide primers extending from the first portion of the plurality of barcode sequences, deprotecting the second portion of the plurality of barcode sequences by removing the second protecting group, and synthesizing a plurality of second oligonucleotide primers extending from the second portion of the plurality of barcode sequences. In this manner, distinct primer sequences can be synthesized on the same substrate without damaging either primer in the process. In some cases, any of the first or second oligonucleotide primers can be capped at any point in creating the capture complexes of the capture substrate. In one specific example, the terminal ends of the first oligonucleotide primers can be capped prior to deprotecting the second portion of the plurality of barcode sequences. Additionally, depending on the nature of the molecules of interest, the first and second oligonucleotide primers can be sequenced 5' to 3' or 3' to 5'.

Generally, protecting the first and second portions of barcode sequences can be accomplished by a variety of protection techniques, which are not limiting. In one example, such protection can include reacting the plurality of barcode sequences with a mixture including first nucleoside building blocks including the first protecting group, and second nucleoside building blocks including the second protecting group. In this case, the first portion of the plurality of barcode sequences is a result of reaction with the first nucleoside building blocks, and the second portion of the plurality of barcode sequences is a result of reaction with the second nucleoside building blocks. It is contemplated that any compatible building block can be utilized as described. Such can include, for example, nucleoside and nonnucleoside moieties, including nucleoside phosphoramidites, non-nucleoside phosphoramidites, various nucleotides, or other molecule having a sugar-phosphate backbone.

In one further example, the plurality of first oligonucleotide primers and the plurality of second oligonucleotide primers are configured to capture specific first molecules of interest and specific second molecules of interest having a functional relationship with one another. In other examples, one of the plurality of first oligonucleotide primers or the plurality of second oligonucleotide primers is configured to capture a specific molecule of interest, and the other of the plurality of first oligonucleotide primers or the plurality of second oligonucleotide primers is configured to capture nonspecific molecules. As a specific example, one primer can be configured to capture a specific mRNA, and the other primer can be configured to capture non-specific mRNA. In this case, the first primer is specifically complementary to a portion of the specific mRNA, and the second primer includes a non-specific sequence that captures a mRNA by, for example, a poly A tail. By using a small number of primers to capture the mRNA of interest, and a large number of non-specific primers, expression of the specific mRNA can be compared against a large portion of the mRNA expression from the cell or cells.

The following demonstrates that two different capture sequences can be built onto a single bead, enabling specific capture and amplification of mRNAs encoding the heavy and light chains of an antigen receptor. However, it should be understood that the number of capture sequences per bead is not so limited. Furthermore, drop-seq techniques are known, and incorporating the presently disclosed technology into a given drop-seq protocol is well within the abilities of one of ordinary skill in the art, once in possession of the present specification. It is noted, however, that the present scope is not limited to drop-seq technologies, and that any solid support strategy compatible with the presently disclosed techniques are contemplated. One non-limiting example can include the Fluidigm® C1 cell genomics system.

Capture beads having different primer sequences could be generated by chemical attachment of the primers to beads. However, one useful component of single-cell analysis techniques is the incorporation of unique barcodes on each bead, located upstream from the primer sequence. This enables, for example, >$10^8$ reads acquired from NGS to be re-grouped into populations arising from each individual cell. The barcoded beads can be generated using split-pool combinatorial synthesis, and thus the primer sequences are synthesized directly onto the barcode sequence, such that the entire sequence is amplified and read in NGS. An additional consideration for such capture beads is that the DNA is synthesized in the "reverse" 5'-3' direction, as this provides the 3' terminus that is needed for enzymatic primer extension after mRNA capture.

Figure 2:
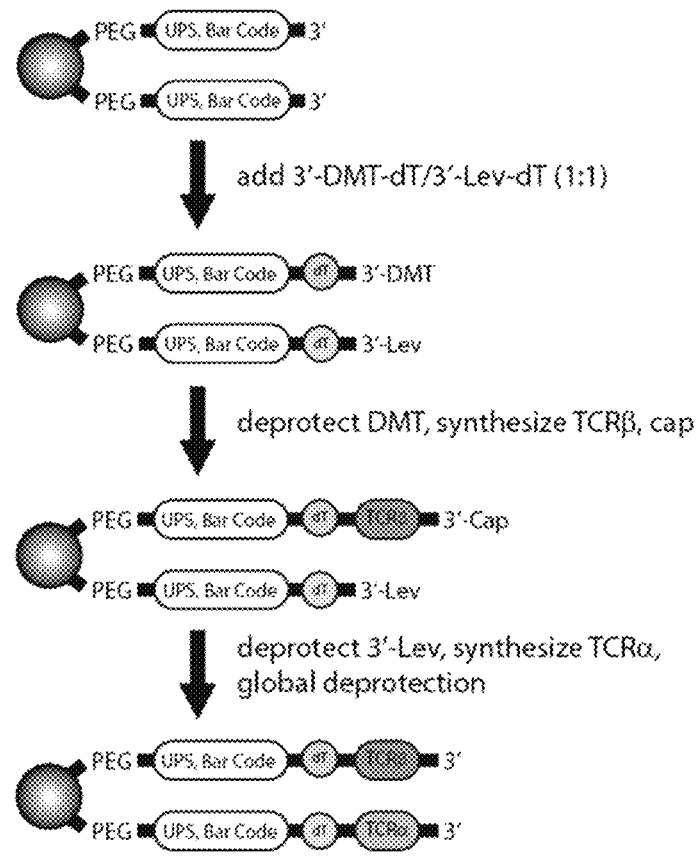
FIG. 2 is schematic illustrating steps in generating a capture substrate having two distinct capture molecules in accordance with an embodiment of the present disclosure.

FIG. 2 shows one example of a split-pool synthesis technique that can be used to make capture beads having two or more different capture molecules coupled thereto. Beads can be synthesized with unique barcodes that can be keyed to a variety of assay elements/metrics, non-limiting examples of which can include a specific bead, a population of beads, populations between individual subjects in, for example, pooled samples, bifurcated sequences produced on a solid support, and the like. Protecting groups can then be added to the beads in order to differentially protect at least two populations of barcodes across the mixture of capture beads. For example, a mixture of 5' phosphoramidite monomers having different protecting groups at the 3' position can be reacted with the mixture of capture beads, thus generating a number of populations of barcodes corresponding to the number of different 3' protecting groups. This would enable selective deprotection of a first population of the oligonucleotides followed by synthesis of a first primer sequence. A second population of the oligonucleotides can then be deprotected, followed by synthesis of a second primer sequence. This process can thus be repeated for any remaining protected populations. Moreover, one of the deprotected chains can be subsequently reacted with a mixture of all of the differentially protected phosphoramidites, and the process of selective deprotection and chain synthesis repeated. In this way, the total number of sequences on each bead can exceed the number of protecting groups used.

To create a two-population capture bead system, for example, a mixture of 3'-dimethoxytrityl (DMT) and 3'-levulinyl (Lev) phosphoramidites can be utilized to enable stepwise synthesis of two different oligonucleotides. DMT can be removed under mildly acidic conditions, while Lev is deprotected using aqueous hydrazine. It can be useful to consider the following in the selection of protecting groups that will be used together. First, the second protecting group should be stable to the deprotection conditions of the first protecting group. Second, all protecting groups should be stable to conditions used for oligonucleotide synthesis, or to the synthesis or coupling chemistry of whatever capture molecules are being used. And third, the protecting groups should be capable of deprotection under conditions that are compatible with capture molecule synthesis.

Protecting group moieties can be added at any useful ratio, which can vary depending on experimental design, reactivity or other nature of associated capture molecule, and the like. In one embodiment, for example, two protecting groups can be added to the bead mixture at 1:1, which generally allows a similar number of each protecting group to be present on each bead. The ratios can thus be adjusted to vary the proportions of bead surface associated with a given protecting group, as described above. Such also applies to the use of 3 or more protecting groups applied to a single substrate.

Figure 3:
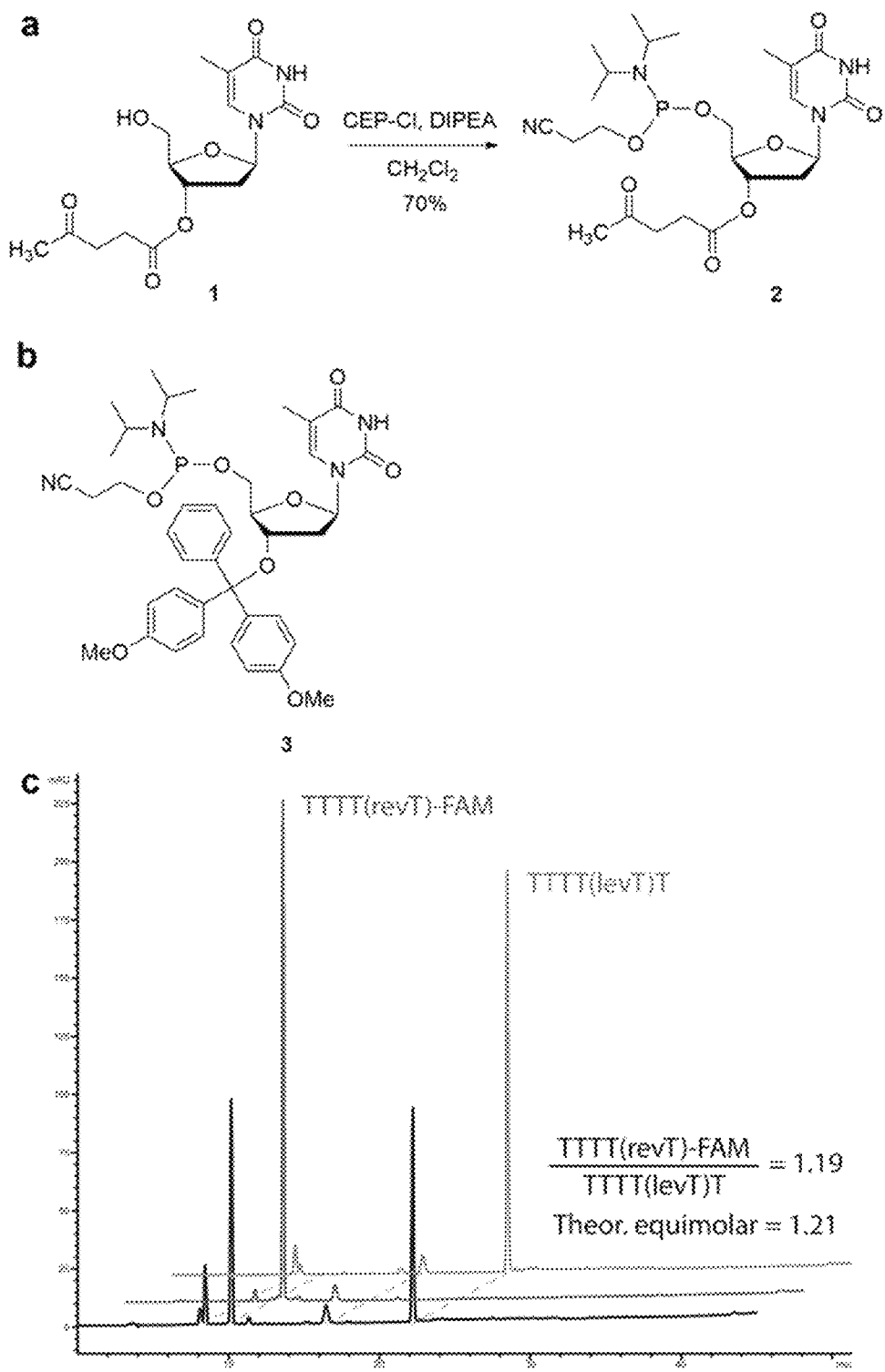
FIG. 3A shows an example synthesis of 3'-OLev thymine phosphoramidite in accordance with an embodiment of the present disclosure.
FIG. 3B shows the chemical structure of a DMT-protected monomer in accordance with an embodiment of the present disclosure.
FIG. 3C shows HPLC traces of test sequences synthesized in tandem on the same substrate in accordance with an embodiment of the present disclosure.

FIG. 3 shows a non-limiting example synthesis of 3'-OLev thymine phosphoramidite (compound 2) from commercially available compound 1 using standard protocols. A synthesis of short polyT sequences was performed to test the compatibility of compound 2 with a divergent oligonucleotide synthesis protocol. To mimic synthesis of the barcode region, four thymine monomer coupling steps were performed on all beads. A 1:1 mixture of 3'-ODMT monomer (compound 3) and 3'-OLev monomer (compound 2) was added, and then the DMT group was removed, and the deprotected oligonucleotide chains were coupled with a fluorescein phosphoramidite. Next, the Lev group was removed using aqueous hydrazine, and the resulting deprotected oligonucleotide chains were coupled with an additional thymine monomer. Both oligonucleotide chains were then cleaved from the beads and analyzed by HPLC. As shown in FIG. 3b, the ratio between $T_5$-FAM DNA (arising from addition of compound 3) and $T_6$ DNA (arising from addition of compound 2) is very close to 1:1, demonstrating that the two different monomers are added to a growing oligonucleotide chain with nearly equal efficiency. Additionally, the high purity of the DNA products obtained indicates that the Lev protecting group is not removed during DMT removal or the subsequent coupling step, and that deprotection of the Lev group does not damage the DNA molecules.

FIG. 3A shows the synthesis of the Lev-protected monomer 2, FIG. 3B shows the chemical structure of DMT-protected monomer 3; and FIG. 3C shows HPLC traces of test sequences synthesized in tandem on the same beads. Black trace shows product cleaved from beads. Blue and red traces show individually synthesized products arising from coupling of 2 and 3, respectively.

In another example, a capture system precursor is provided. Such a precursor can include a capture substrate, and a plurality of capture complexes coupled to the capture substrate. Each capture complex further includes a barcode sequence, a linker molecule coupled to the barcode sequence, and a protecting group coupled to the linker molecule, where the protecting group is one of a plurality of protecting groups. The plurality of capture complexes includes at least a first population and a second population of linker molecules, each population having a different protecting group. In one example, the linker molecule is a nucleoside building block. In another example, the nucleoside building block is a nucleoside phosphoramidite. Regarding protecting groups, any protection chemistry, reaction, molecule, or the like, is considered to be within the present scope. In one example, the first population of linker molecules includes a DMT protecting group. In another example, the second population of linker molecules includes a Lev protecting group.

The present disclosure also provides various assays and methods of use. For example, in one embodiment a method of extracting multiple distinct groups of specific nucleotide sequences from a multisource aggregation of biological material is provided, where the specific nucleotide sequences in each distinct group are from a single specific source of the multisource aggregation. A source is defined as a specific source of biological material for this there is a benefit to maintaining an association between specific biological material extracted therefrom, throughout processing and analysis. In one example, a source can be a single cell. In another example, a source can be a single cell type. In other examples, a source can be a non-natural pool of biological material, such as a sample defined in a laboratory. The aforementioned method can include, in each of a plurality of single specific source reactions, incubating a plurality of capture substrate-linked first and second oligonucleotide primers with a single specific source of biological material to allow capture of corresponding first and second nucleotide sequences from only the biological material of the single specific source. Such isolation can be accomplished by any technique that allows incubation and processing of biological material from a single source, including, without limitation, drop-seq techniques. Following capture of the nucleotide sequences, the method further includes synthesizing to extend the first and second oligonucleotide primers using the first and second nucleotide sequences as templates to generate first and second synthetic nucleotides. The various single specific source reactions can then be aggregated into a multisource aggregation for further processing. The aggregated capture substrates from the multisource aggregation can be isolated, using any type of extraction technique, such as magnetic techniques, washing, column separation, centrifuging, and the like, as well as combinations thereof. Following isolation, the first and second synthetic nucleotides are cleaved from the capture substrates, and grouped according to the associated barcode sequences to create a distinct group for each single specific source. In some examples, the synthetic nucleotide sequences can be amplified to increase the yield of the first and second nucleotide sequences.

Figure 4:
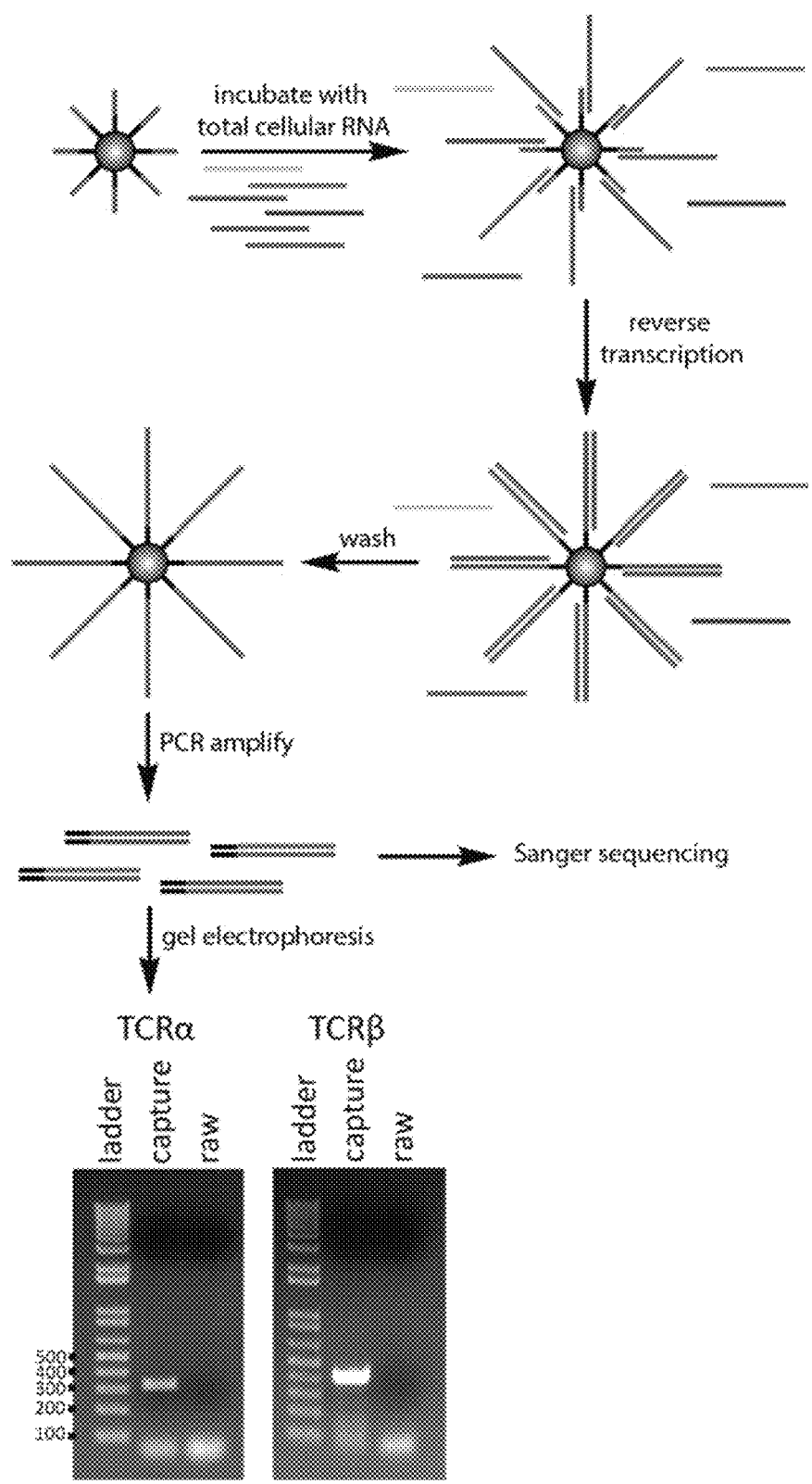
FIG. 4 shows the generation of dual-primer beads for capture and amplification of mRNAs encoding the α and β chains of the T cell antigen receptor in accordance with an embodiment of the present disclosure.
Figure 8:
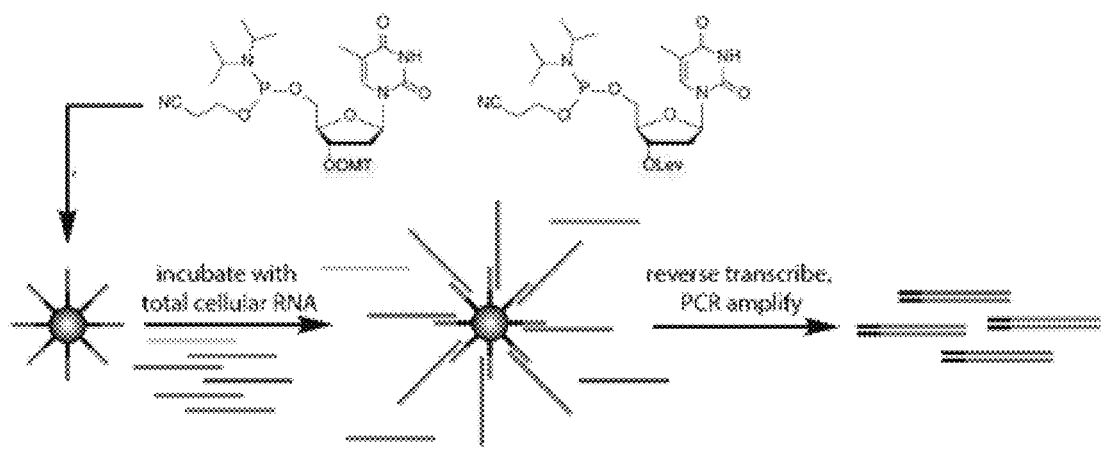
FIG. 8 shows the generation of dual-primer beads for capture and amplification of mRNAs using DMT and OLev protecting groups in accordance with an embodiment of the present disclosure.

Returning to the T cell example, having established that Lev can function as a DNA-compatible orthogonal protecting group, dual-primer beads were generated for capture and amplification of mRNAs encoding the α and β chains of the T cell antigen receptor (see FIG. 4 and FIG. 8). Using the same synthetic test protocol described above, beads capable of targeting both the T cell receptor alpha chain (TCRα) and beta chain (TCRβ) mRNAs were synthesized specifically to capture the mRNA adjacent to the region where sequence diversity exists so that subsequent sequencing would identify this highly variable region. Specifically, the capture sequences attached to the beads are complementary to the TCRα and TCRβ constant regions (TRAC and TRBC). To test the ability of the capture beads to pull down TCR mRNA, the beads were mixed with total RNA isolated from a known T cell clone (clone GDB4). Unbound RNA was removed by washing, and the bead-bound RNA was subjected to a reverse transcription reaction in which the DNA oligonucleotides attached to the beads served as primers for the synthesis of bead-bound cDNA. PCR amplification of the cDNA was then performed using primers complementary to the known sequence of the T cell receptor alpha and beta chain transcripts in the GDB4 clone. As a control, all of the above steps were also carried out using "raw" beads, on which no DNA had been synthesized. FIG. 4 shows an agarose gel image of the PCR product from each reaction, which demonstrates amplification of the TCRα and TCRβ sequences when using the capture beads, but not with the raw beads. The bands corresponding to the PCR products were excised from the gel and subjected to Sanger sequencing. The sequencing results shown in the Examples section below are consistent with the known TCRα and TCRβ sequences in the GDB4 clone, confirming the ability of the capture beads to pull down TCR mRNA.

As illustrated in FIG. 4, RNA from lysed T cells was incubated with capture beads having sequences complementary to the constant region of TCRα and TCRβ. Captured RNA was reverse transcribed and PCR amplified, then resolved using gel electrophoresis and visualized by ethidium bromide staining. PCR reactions from the capture beads show amplification of TCRα and TCRβ sequences. As a control, all of the above steps were performed using raw beads (no oligos attached), and show no PCR product. The size (in base pairs) of the smallest five bands in the DNA ladder are indicated to the left of the first gel image.

Figure 5:
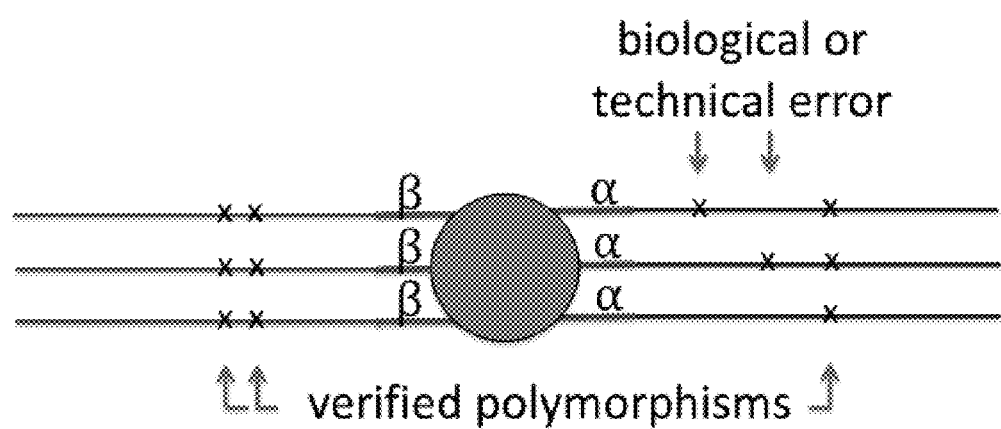
FIG. 5 shows a schematic illustrating redundancy in the sequencing process to discriminate real polymorphisms from transcriptional or sequencing errors in accordance with an embodiment of the present disclosure.

As such, beads containing unique oligonucleotide barcodes followed by two independent oligonucleotide capture sequences can be produced. These beads can be used to capture two different specific target sequences, which has high utility in cases such as the T-cell antigen receptor, where receptor chain pairing is critical for determination of antigen specificity, but is highly variable at the single cell level. Importantly, each bead can have any number of copies of the capture sequence, such as, for example 5000 or more. This provides redundancy in the sequencing process to discriminate real polymorphisms from transcriptional or sequencing errors (see FIG. 5). FIG. 5 shows that multiple copies of α and β chain mRNAs can be captured from each cell by individual beads. Alignments of redundant sequencing reads from each bead allows discrimination between true polymorphisms and sequencing or transcriptional errors.

One technique for achieving synthesis of the two different oligonucleotide sequences on a single bead is the use of a 3'-Lev-protected phosphoramidite, which is stable to the conditions used for DMT deprotection and oligonucleotide synthesis, and can be subsequently removed without damaging the newly formed oligonucleotides. While the example above utilizes a single differential protection step, the divergent DMT/Lev protection step can be used iteratively to generate beads having larger numbers of unique DNA capture sequences. Further diversity can be achieved by utilizing additional protecting groups and protecting techniques. This synthesis scheme may also be used to produce capture reagents that can be used as biological probes when linked to sequences that include molecular dyes that can be specifically visualized or quenched.

The immense diversity of the adaptive immune system relies on production of several antigen receptor types, on both B-cells and T-cells, that are synthesized from transcripts that have undergone germline rearrangements. Identifying these germline rearrangements is only possible through direct sequencing of the corresponding DNA or mRNA. As the complexity of the adaptive immune response continues to expand, abhorrent immune responses have been identified as the basis for several diseases. These diseases can arise from a single clone, and thus the ability to obtain paired sequence information for antigen receptor heavy and light chains at the single cell level would be transformative in identifying these diseases causing autoimmune clones.

It is noted that further strategies for capturing and associating greater numbers of molecules of interest from a single source of biological material are contemplated, such as adding further capture complexes having distinct molecules to the capture substrate beyond two, as described above. In other examples, doublers, treblers, and the like, can be used in various capture complexes to couple multiple capture molecules together throughout one or more downstream processes, even following cleavage of the capture complexes from the capture substrate.

Further information regarding drop-seq techniques, can be found in "Drop-Seq Laboratory Protocol, version 3.1 (12/28/15), Evan Macosko and Melissa Goldman, Steve McCarrol Lab, Harvard Medical School, available at mccarrolllab.com/dropseq/, which is incorporated herein by reference.

EXAMPLES

Examples of various experimental details are described to provide a fuller understanding of the presently disclosed technology, and are not intended to be limiting.

General

Unless otherwise noted, all starting materials were obtained from commercial suppliers and were used without further purification. Flash column chromatography was carried out using silica gel 60 (230-400 mesh). $^1$H NMR and $^{31}$P NMR chemical shifts are expressed in parts per million ($\delta$). Mass spectra were obtained through the Mass Spectrometry Core Facility, University of Utah.

Synthesis of Phosphoramidite (Compound 2, Equation I)

Figure 6:
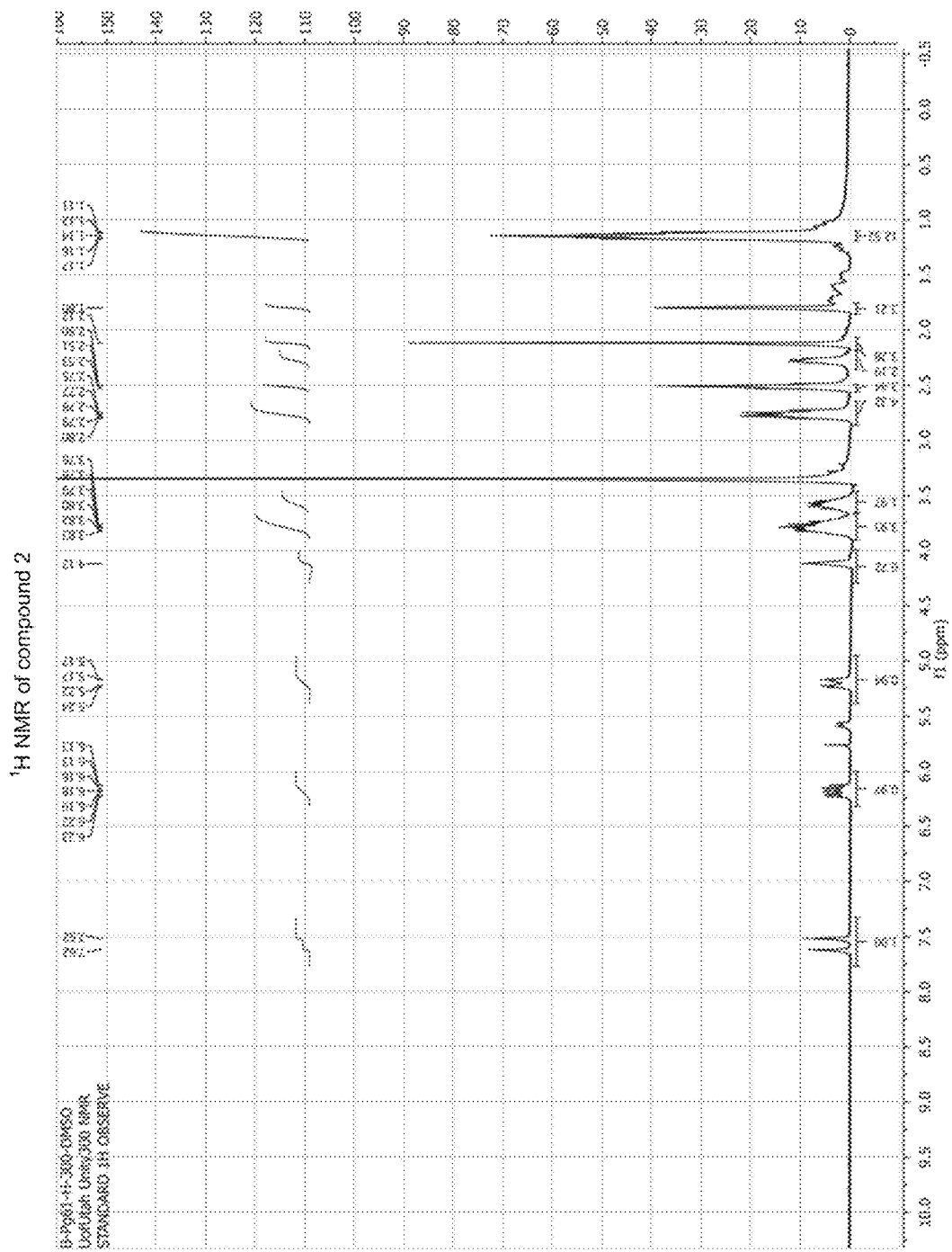
FIG. 6 shows $^1$H NMR data for compound 2 in accordance with an embodiment of the present disclosure.
Figure 7:
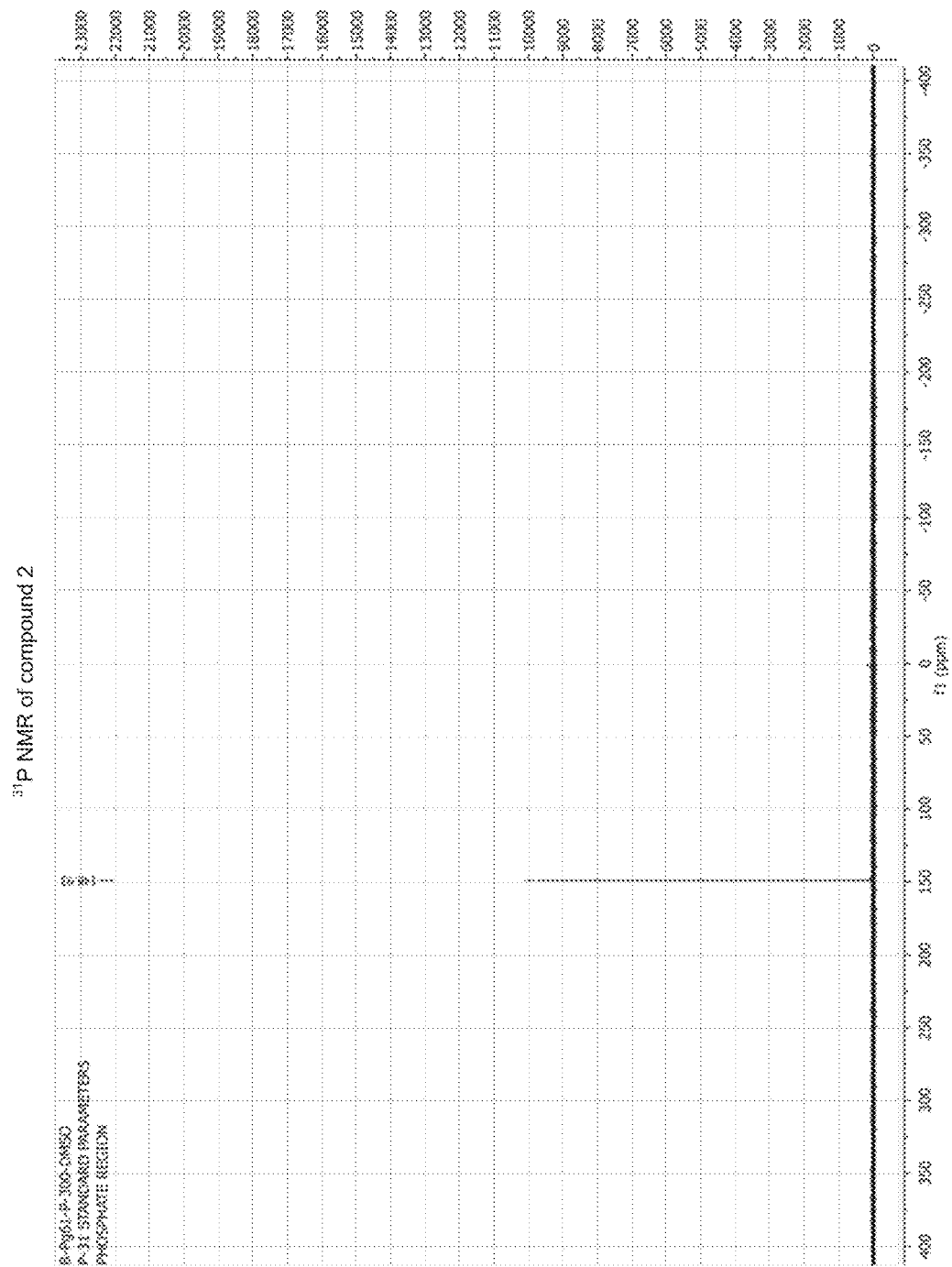
FIG. 7 shows $^{31}$P NMR data for compound 2 in accordance with an embodiment of the present disclosure.

To a solution of compound 1 (225 mg, 0.66 mmol) and DIPEA (0.2 mL, 1.20 mmol) in anhydrous CH$_2$Cl$_2$ (4 mL) was added 2-cyanoethyl N,N-diisopropylchlorophosphoramidite (CEP-Cl, 0.17 mL, 0.73 mmol), and the reaction mixture was stirred under N$_2$ at room temperature. After 45 min, thin-layer chromatography (TLC) showed the disappearance of compound 1, so the reaction mixture was diluted with CH$_2$Cl$_2$ (150 mL), washed with 10% NaHCO$_3$ (2×30 mL), dried over Na$_2$SO$_4$, filtered, and evaporated under reduced pressure. The crude product was purified by silica gel column chromatography (1:1 hexanes:EtOAc, then 99:1 EtOAc:Et$_3$N) to give compound 2 as a colorless syrup (250 mg, 70%); R$_f$=0.6, (99:1 EtOAc:Et$_3$N). $^1$H NMR (300 MHz, DMSO-d$_6$, see FIG. 6) $\delta$ 7.62, 7.52 (s, two single peaks, total 1H), 6.23-6.13 (m, 1H), 5.24-5.17 (m, 1H), 4.12 (s, 1H), 3.83-3.74 (m, 2H), 3.62-3.54 (m, 4H), 2.80-2.73 (m, 4H), 2.53-2.49 (m, 3H), 2.30-2.26 (m, 2H), 2.12 (s, 3H), 1.80 (s, 3H), 1.17-1.11 (m, 12H); $^{31}$P NMR (121 MHz, DMSO-d$_6$ see FIG. 7) $\delta$ 148.9.

Synthesis I

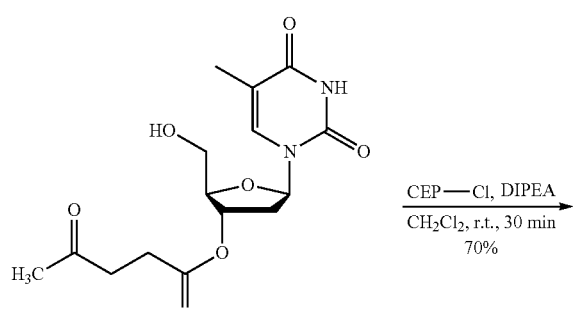

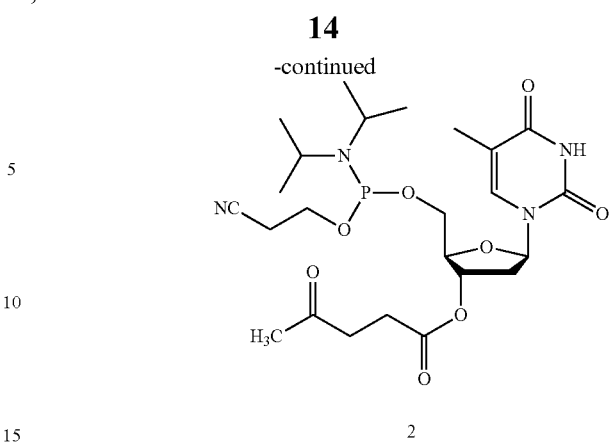

Oligonucleotide Synthesis Using Monomers 2 and 3

All DNA synthesis was performed using standard phosphoramidite chemistry and reagents using an ABI 394 synthesizer.

The sequence (DMT-5'-TT/FAM-3'-T)TTTT-3' was synthesized using standard 3'-DMT monomers and 0.2 µmole polystyrene supports (Glen Research). 3'-ODMT-dT and 3'-OLev-dT monomers were dissolved to 100 mM in anhydrous acetonitrile and coupled to the growing poly-dT chain in a 1:1 mixture for 15 minutes. After standard detritylation, 6-carboxyfluorescein phosphoramidite (Glen Research 10-1964) was then added, followed by DMT-removal and a 5 minute capping reaction using standard reagents (acetic anhydride/N-methylimidazole). Levulinyl deprotection solution (ChemGenes) was then used to remove 3'-levulinyl groups from the remaining thymidine bases, and another 5'-ODMT-dT was coupled to the newly generated 3'-OH groups. The final products were cleaved from the solid support for 1 hour in 30% ammonium hydroxide at room temperature and deprotected for 1 hour at 65° C. The DNA oligomers were then dried under vacuum and dissolved in 0.1 M triethylene acetate for HPLC analysis. Reversed-phase HPLC analysis was performed on a Hewlett Packard Series 1100 system with a 5 mm, 250×4.6 mm Higgins Proto 200 C$_{18}$ column equilibrated to 40° C., with 39 min linear gradient from 2% to 80% mobile phase. The stationary phase solution was 5% acetontirile, 20 mM triethylamine acetate and the mobile phase was 80% acetontirile, 20 mM triethylamine acetate. To confirm peak identities, independent syntheses of 3'-TTTT(3'-ODMT-T)-3'-FAM and 3'-TTTT(3'-OLev-T)T-5'-DMT were carried out, and those products analyzed using the same HPLC protocol.

Capture bead synthesis was performed on the 1 µmole scale using Toyopearl HW-65S beads (Tosoh Bioscience) as solid-phase support. Except where noted, 1 min detritylation, 1 min coupling, 30 s capping, and 25 s oxidation times were used, along with 3'-DMT/5'-phosphoramidite monomers (Glen Research). 20 mg of HW-65S beads were first derivitized with Spacer18 phosphoramidite (Glen Research 10-1918) using three separate 15 min coupling reactions. Any remaining bead hydroxyl groups were blocked using four 10 min capping reactions with standard acetic anhydride/N-methylimidazole synthesis reagents. The following sequence was then synthesized after removal of the ethylene glycol DMT groups:

(SEQ ID NO: 01)
5'TTTTTTTAAGCAGTGGTATCAACGCAGAGTACJJJJJJJJJJJJJ
NNNNNNNNTGGTGAATAGGCAGACAGACTTGTC3' and -continued

```
5'TTTTTTTAAGCAGTGGTATCAACGCAGAGTACJJJJJJJJJJJJ
NNNNNNNNNTGAGACCCTCAGGCGGCTG CT3'
```

(SEQ ID NO: 02), degenerate N positions comprise the molecular identifier region, and J residues are bar code positions (either dA, dG, dC, or dT).

First, the bar code region was synthesized according to the split-pool protocol described by Macosko, et al (Cell 2015, 161, 1202; incorporated herein by reference), using 5 mg of beads for each monomer in each synthesis cycle. After bar code synthesis, all 20 mg of beads were recombined, and 10 mg of the bar coded bead pool were used for synthesis of the molecular identifier and TCR sequences. After the addition of the molecular identifier sequence, a single coupling step was used to incorporate a 1:1 mixture of 3'-ODMT-dT and 3'-OLev-dT (15 min coupling). Upon trityl deprotection, TCRβ synthesis was performed and finalized with a 2 min detritylation and 5 min capping step. Finally, the 3'-levulinyly groups were removed, and the TCRα sequence was synthesized, followed by removal of the ultimate 3'-trityl groups. The completed beads were deprotected in 30% ammonium hydroxide for 20 h at room temperature, washed with acetonitrile, and dried under vacuum.

RNA Capture, Reverse Transcription, and PCR[1]

Capture beads (beads derivatized with T-Cell-specific capture oligos) and raw beads (beads with no capture oligo) were prepared by washing with ethanol and TE-TW (TE buffer with 0.01% Tween 20). Prepared beads were counted and washed in water. For RNA capture and reverse transcription, 2,100 beads of each type were mixed in parallel with 20 ng of total RNA isolated from T cell clones, and subjected to a reverse transcription reaction. Specifically, solutions containing beads, RNA and 1 mM dNTP (6 µL total volume) were heated to 65° C. for 5 min and then chilled on ice to denature any RNA secondary structure. A Maxima H-Reverse transcriptase mixture (1× Maxima RT Buffer, 1 mM dNTPs, 4% Ficoll PM-400, 1 U RNase Inhibitor (Lucigen), 2.5 uM Template Switch Oligo[1] and 10 U of Maxima H Minus Reverse Transcriptase (Thermo Scientific)) was added to the denatured bead/RNA/dNTP solutions, bringing the mixtures to a total volume of 100 µL. Bead/RNA/reverse transcriptase mixtures were incubated for 30 min at room temperature followed by >90 min at 42° C. Subsequently, beads were washed in TE-SDS (TE buffer with 0.5% SDS) and twice with TE-TW, and then treated with Exonuclease I (ExoI, New England Biolabs) at 37° C. for 45 minutes. Following ExoI treatment, beads were once again washed in TE-SDS and twice with TE-TW. The ExoI step was skipped for the TCRβ set.

PCR amplification was used to establish capture of TCRα and TCRβ RNA transcripts by the beads. Each set of treated beads was divided equally into four tubes to allow for multiple reactions, and each aliquot of beads was washed in water. Approximately 500 beads were used per PCR reaction. Thermo Scientific Phusion High-Fidelity PCR master mix was added to each set of beads along with 0.5 µM of each primer, and the mixture was annealed by incubating at 58° C. The TCRα cDNA was PCR amplified using TRAV and capture_a_nested primers over 47 cycles. The TCRβ cDNA was PCR amplified using TRBV and capture_b_nested primers over 30 cycles, followed by AMPure XP PCR purification (Beckman Coulter) and a second round of PCR amplification using TRBV nested and capture_b_nested primers for 35 cycles. Equal volumes of PCR samples were separated using 1% agarose gels and visualized by ethidium bromide staining. 1 kb-Plus DNA ladder (Thermo Fisher Scientific) was used to determine PCR product size. PCR bands were cut out, purified, and the identity of TCRα and TCRβ PCR bands were confirmed by Sanger sequencing.

TABLE 1

| Primer sequences (5'-3') | | |
|---|---|---|
| TRAV | GCACATATGACACCAGTGAG | SEQ ID NO: 03 |
| capture_a_nested | AGAGTCTCTCAGCTGGTACACG | SEQ ID NO: 04 |
| TRBV | ACTACACCTCATCCACTATTCC | SEQ ID NO: 05 |
| TRBVnested | CAGAGAAGGGAGATCTTTCC | SEQ ID NO: 06 |
| capture_b_nested | AGGCAGTATCTGGAGTCATTGAG | SEQ ID NO: 07 |

Sequencing results for PCR products amplified from mRNA captured from clone MC.7G5.57 are shown in Table 2. TCR-α included TRAV38.DV2 variable and TRAJ31 joining genes. TCR-β included TRBV25.1 variable and TRBJ2.3 joining genes. Sequences corresponding to variable (green), joining regions (blue), CDR3 regions (pink) and constant regions (black) are shown. The sequences of the CDR3 regions were exact matches for cDNA from the expected clone: MC.7G5.57.

TABLE 2

| | Sequence of PCR products from capture |
|---|---|
| TCR-α<br>SEQ ID NO: 08 | CGTTTCTCTGTGAACTTCCAGAAAGCAGCCAAATCCTTCAGTCTCAAGATCT<br>CAGACTCACAGCTGGGGGATGCGCGATGTATTTCTGTGCTTATAGGAGCG<br>CGGTCAATGCCAGACTCATGTTTGGAGATGGAACTCAGCTGGTGGTGAAGC<br>CCAATATCCAGAAGCCTGACCCTGCCGTGTACCA |
| TCR-β<br>SEQ ID NO: 09 | TTTTCCCCTGACCCTGGAGTCTGCCAGGCCCTCACATACCTCTCAGTACCTC<br>TGTGCCAGCAGTGAAGCTCGGGGGTAGCGGAGTTCACAGATACGCAGTA<br>TTTGGCCCAGGCACCCGGCTGACAGTGCTCGAGGACCTGAAAAACGTGTT |

TABLE 2-continued

Sequence of PCR products from capture

```
CCCACCCGAGGTCGCTGTGTTTGAGCCATCAGAAGCAGAGATCTCCCACACC
CAAAAGGCCACACTGGTGTGCCTGGCCACAGGCTTCTACCCCGACCACGTG
GAGCTGAGCTGGTGGGTGAATGGGAAGGAGGTGCACAGTGGGGTCAGCACA
GACCCGCAGCCCCTCAAGGAGCAGCCCGCCCTCAATGACTC
```

Synthesis of a Doubler Having Lev and DMT Protecting Groups

In some examples, doublers, treblers, and the like, can be used in various capture complexes to couple multiple capture molecules together throughout one or more downstream processes, even following cleavage of the capture complexes from the capture substrate. The following is one example of the synthesis of a doubler having Lev and DMT protecting groups.

Figure 9:
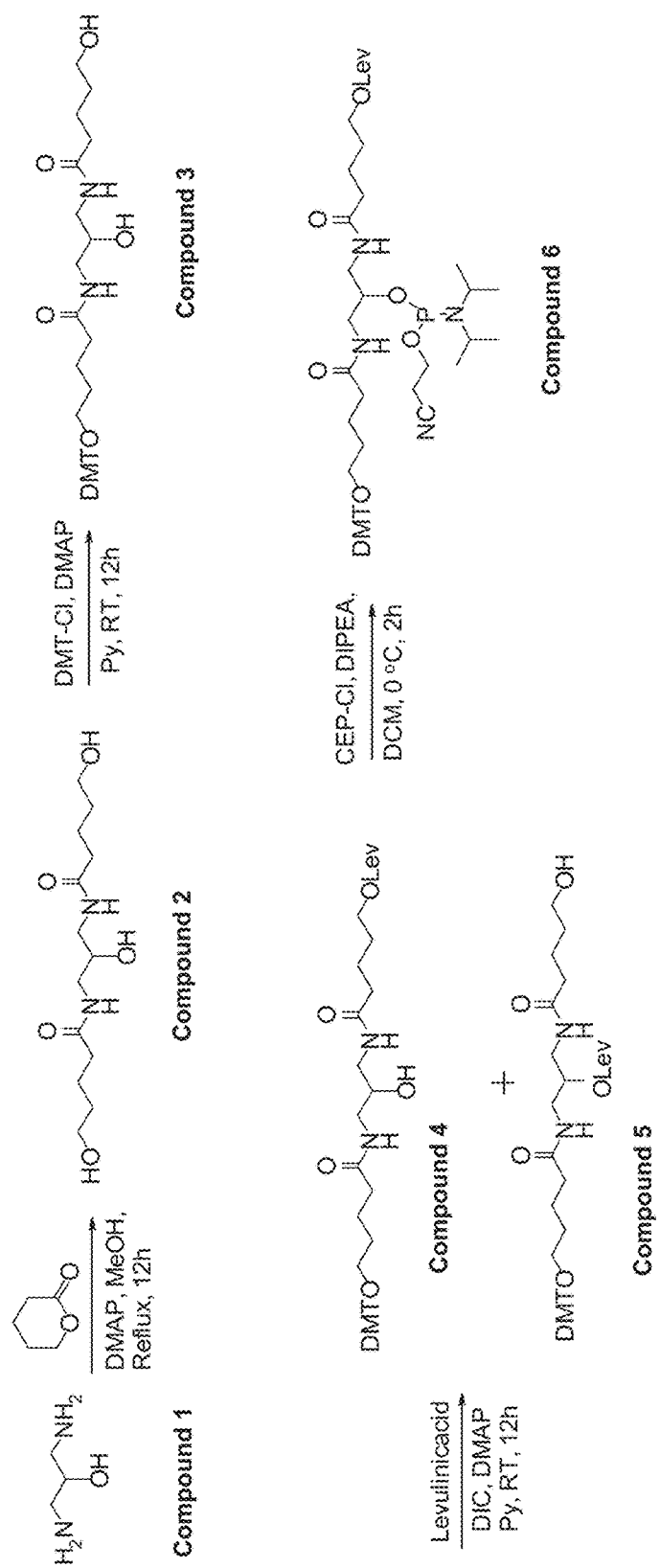
FIG. 9 shows the synthesis of a doubler having Lev and DMT protecting groups in accordance with an embodiment of the present disclosure.

Synthesis of N,N'-(2-hydroxypropane-1,3-diyl)bis(5-hydroxypentanamide (Compound 2, FIG. 9). To a solution of compound 1 (3.5 g, 38.88 mmol) in methanol (25.0 mL), DMAP (190.0 mg, 1.55 mmol) and δ-valeroloctone (7.9 mL, 85.55 mmol) were added at room temperature and refluxed for 12 h, monitoring the completion of reaction by TLC. After completion of the reaction, the solvent was removed in vacuo, and the product was precipitated from 25.0 ml of DCM at 4° C. to give compound 2 as a white powder (9.0 g, 79% yield): $^1$H-NMR (300 MHz, CD$_3$OD) δ: 1.54-1.67 (m, 8H), 1.22-2.35 (m, 4H), 3.21-3.24 (m, 2H), 3.54-3.58 (m, 4H), 3.71-3.73 (m, 1H); $^{13}$C-NMR (100 MHz, CD$_3$OD) δ: 16.7, 21.3, 22.2, 31.8, 31.9, 33.3, 35.6, 42.9, 47.0, 47.3, 47.6, 47.9, 48.2, 48.4, 48.7, 61.2, 61.3, 69.1; LRMS (ESI-TOF) m/z: [M]$^+$ Calcd for C$_{13}$H$_{25}$N$_2$O$_5$ 290.18; Found 289.5.

Synthesis of 5-(bis(4-methoxyphenyl)(phenyl)methoxy)-N-(2-hydroxy-3-(5-hydroxypentanamido)propyl)pentanamide (Compound 3, FIG. 9). To a solution of compound 2 (4.0 g, 13.79 mmol) in pyridine (25.0 mL), DMAP (670.0 mg, 5.52 mmol) and DMT-Cl (4.7 g, 13.79 mmol) were added at room temperature, and stirred at the same temperature for 12 h. After completion of reaction, the solvent was removed in vacuo and the product was purified using column chromatography, eluting with 10% MeOH/DCM to obtain compound 3 as a sticky solid (3.0 g, 37% yield). $^1$H-NMR (300 MHz, CDCl$_3$) δ: 1.53-1.71 (m, 8H), 2.15-2.25 (m, 4H), 3.03 (t, J=6 Hz, 2H), 3.14-3.33 (m, 4H), 3.43 (s, 2H), 3.58-3.60 (m, 2H), 3.69-3.71 (m, 1H), 3.75 (s, 6H), 4.83 (bs, 1H), 6.78-6.81 (m, 4H), 7.27-7.39 (m, 9H); $^{13}$C-NMR (75 MHz, CDCl$_3$) δ: 22.1, 22.8, 29.8, 32.0, 36.1, 36.5, 42.6, 55.4, 62.1, 63.1, 76.8, 77.3, 77.7, 86.0, 113.2, 126.9, 127.9, 128.4, 130.2, 136.7, 145.4, 158.5, 175.2. LRMS (ESI-TOF) m/z: [M+Na]$^+$ Calcd for C$_{34}$H$_{44}$N$_2$NaO$_7$ 615.30; Found 615.4.

Synthesis of 5-((3-(5-(bis(4-methoxyphenyl)(phenyl)methoxy)pentanamido)-2-hydroxypropyl)amino)-5-oxopentyl 4-oxopentanoate (Compound 4, FIG. 9). To a solution of compound 3 (3.0 g, 5.07 mmol) in pyridine (25.0 mL), DMAP (620.0 mg, 5.07 mmol), DIC (1.4 mL, 10.14 mmol) and levulinic acid (880.0 mg, 7.601 mmol) were added at room temperature and stirred at the same temperature for 12 h. After completion of reaction, the solvent was removed in vacuo and the product was extracted with DCM (3×25). The organic layer was dried over anhydrous Na$_2$SO$_4$ and purified using column chromatography, eluting with 2% MeOH/DCM to obtain compound 4 as a sticky solid (1.4 g, 40% yield). $^1$H-NMR (300 MHz, CDCl$_3$) δ: 1.63-1.72 (m, 8H), 2.16-2.27 (m, 7H), 2.55 (t, J=6 Hz, 2H), 2.75 (t, J=6 Hz, 2H), 3.07 (t, J=6 Hz, 2H), 3.21-3.38 (m, 4H), 3.72-3.75 (m, 1H), 3.79 (s, 6H), 4.10 (t, J=6 Hz, 2H), 6.26 (bs, 1H), 6.49 (bs, 1H), 6.82 (d, J=9 Hz, 4H), 7.19-7.32 (m, 7H), 7.42 (d, J=9 Hz, 2H); $^{13}$C-NMR (75 MHz, CDCl$_3$) δ: 22.2, 22.6, 27.9, 29.9, 35.8, 36.3, 38.0, 42.8, 55.2, 62.8, 64.0, 70.8, 84.7, 113.0, 126.6, 127.7, 128.1, 130.0, 136.5, 145.2, 158.3; LRMS (ESI-TOF) m/z: [M-H]$^+$ Calcd for C$_{39}$H$_{49}$N$_2$O$_9$ 689.34; Found 689.0.

Characteristics of 1-(5-(bis(4-methoxyphenyl)(phenyl)methoxy)pentanamido)-3-(5-hydroxypentanamido)propan-2-yl 4-oxopentanoate (Compound 5, FIG. 9, side product). $^1$H-NMR (300 MHz, D$_2$O) δ: 1.55-1.74 (m, 8H), 2.13 (s, 3H), 2.16-2.28 (m, 4H), 2.45 (t, J=6 Hz, 2H), 2.74-2.79 (m, 2H), 3.05 (t, J=6 Hz, 2H), 3.24-3.34 (m, 2H), 3.43-3.55 (m, 2H), 3.58-3.63 (m, 2H), 3.76 (s, 6H), 4.78-4.84 (m, J=6 Hz, 1H), 6.55 (bs, 1H), 6.80 (dd, J=6 Hz, 4H), 7.17-7.31 (m, 7H), 7.41 (d, J=6 Hz, 2H); $^{13}$C-NMR (75 MHz, CDCl$_3$) δ: 22.0, 22.9, 28.4, 29.9, 30.0, 32.2, 36.2, 36.7, 38.7, 38.8, 38.9, 55.4, 62.2, 63.1, 71.8, 86.0, 113.2, 126.8, 127.9, 128.4, 130.2, 136.8, 145.5, 158.5, 172.3, 174.3. LRMS (ESI-TOF) m/z: [M-H]$^+$ Calcd for C$_{39}$H$_{49}$N$_2$O$_9$ 689.34; Found 689.2.

Synthesis of 5-((3-(5-(bis(4-methoxyphenyl)(phenyl)methoxy)pentanamido)-2-(((2-cyanoethoxy)(diisopropylamino)phosphaneyl)oxy)propyl)amino)-5-oxopentyl 4-oxopentanoate (Compound 6, FIG. 9). To a solution of the compound 4 (500.0 mg, 0.7246 mmol) in DCM (25.0 mL), DIPEA (0.5 mL, 2.8985 mmol) and chloro phosphoramidite (0.16 mL, 0.7971 mmol) were added at ice cold condition and stirred at the same temperature for 2 h. After completion of reaction, the reaction mixture was diluted with DCM and washed with aq. NaHCO$_3$ solution. The organic layer was dried over anhydrous Na$_2$SO$_4$ and purified on neutralized silica (silica gel was stirred in triethylamine and hexane mixture for 1 h) and product was eluted with 2% MeOH/DCM to obtain compound 6 as a semi solid (300.0 mg, 46% yield). $^1$H-NMR (300 MHz, CDCl$_3$) δ: 1.12-1.21 (m, 16H), 166-1.70 (m, 8H), 2.18.2.25 (m, 6H), 2.55-2.74 (m, 5H), 3.05-3.07 (m, 3H), 3.60-3.85 (m, 12H), 4.06 (t, J=6 Hz, 2H), 6.38-6.57 (m, 2H), 6.80 (d, 4H), 7.26-7.32 (m, 8H); $^{13}$C-NMR (75 MHz, CDCl$_3$) δ: 20.6, 22.1, 22.2, 22.7, 23.5, 24.6, 24.7, 27.9, 28.1, 29.7, 29.9, 35.9, 36.0, 36.5, 36.6, 37.9, 40.5, 42.2, 43.1, 43.3, 55.2, 58.1, 58.4, 62.9, 64.2, 70.6, 70.8, 85.7, 112.9, 126.5, 127.7, 128.1, 130.0, 136.6, 145.3, 158.3, 172.7, 173.6; $^{31}$P-NMR (CDCl$_3$, H$_3$PO$_4$ as external reference) δ: 148.18. LRMS (ESI-TOF) m/z: [M+Na]$^+$ Calcd for C$_{48}$H$_{67}$N$_4$NaO$_{10}$P 913.45; Found 913.6.

While the forgoing examples are illustrative of the principles of various embodiments in one or more particular applications, it will be apparent to those of ordinary skill in the art that numerous modifications in form, usage and details of implementation can be made without the exercise of inventive faculty, and without departing from the principles and concepts of the disclosure.

The invention claimed is:

1. A method of making a multi-probe capture system, comprising:
   synthesizing a plurality of barcode sequences extending from a capture substrate, where the plurality of barcode sequences includes a specific identifier to the capture substrate;
   protecting a first portion of the plurality of barcode sequences with a first protecting group; and
   protecting a second portion of the plurality of barcode sequences with a second protecting group, where the second protecting group is stable under conditions for deprotection of the first protecting group, stable under conditions for oligonucleotide synthesis, and is capable of deprotection under conditions compatible with oligonucleotides.

2. The method of claim 1, further comprising:
   deprotecting the first portion of the plurality of barcode sequences by removing the first protecting group;
   synthesizing a plurality of first oligonucleotide primers extending from the first portion of the plurality of barcode sequences;
   deprotecting the second portion of the plurality of barcode sequences by removing the second protecting group; and
   synthesizing a plurality of second oligonucleotide primers extending from the second portion of the plurality of barcode sequences.

3. The method of claim 2, further comprising capping terminal ends of the plurality of first oligonucleotide primers prior to deprotecting the second portion of the plurality of barcode sequences.

4. The method of claim 2, wherein the plurality of first oligonucleotide primers and the plurality of second oligonucleotide primers are sequenced 5' to 3'.

5. The method of claim 2, wherein protecting the first and second portions of the plurality of barcode sequences cormprises:
   reacting the plurality of barcode sequences with a mixture including:
      first nucleoside building blocks including the first protecting group; and
      second nucleoside building blocks including the second protecting group, wherein the first portion of the plurality of barcode sequences is a result of reaction with the first nucleoside building blocks and the second portion of the plurality of barcode sequences is a result of reaction with the second nucleoside building blocks.

6. The method of claim 5, wherein the first and second nucleoside building blocks are nucleoside phosphoramidites.

7. The method of claim 6, wherein the first protecting group is dimethoxytrityl (DMT).

8. The method of claim 6, wherein the second protecting group is levulinyl (Lev).

9. The method of claim 5, wherein the mixture comprises the first nucleoside building blocks and the second nucleoside building blocks in a ratio of from 1:100 to 100:1.

10. The method of claim 5, wherein the mixture comprises the first nucleoside building blocks and the second nucleoside building blocks in a ratio of from 1:10 to 10:1.

11. The method of claim 5, wherein the mixture comprises the first nucleoside building blocks and the second nucleoside building blocks in a ratio of from 1:4 to 4:1.

12. The method of claim 2, wherein the plurality of first oligonucleotide primers and the plurality of second oligonucleotide primers are configured to capture a specific first mRNA and a specific second mRNA having a functional relationship with one another.

13. The method of claim 2, wherein one of the plurality of first oligonucleotide primers and the plurality of second oligonucleotide primers is configured to capture a specific mRNA, and the other of the plurality of first oligonucleotide primers and the plurality of second oligonucleotide primers is configured to capture nonspecific mRNA.

* * * * *